United States Patent [19]
Patel et al.

[11] Patent Number: 5,948,345
[45] Date of Patent: Sep. 7, 1999

[54] METHOD FOR MAKING MEDICAL BALLOON CATHETER

[75] Inventors: Kaushik A. Patel, Temecula; Samir R. Patel, Fremont; Stephen A. Zimmerman, San Diego, all of Calif.

[73] Assignee: Medtronic, Inc., Minneapolis, Minn.

[21] Appl. No.: 09/002,676

[22] Filed: Jan. 5, 1998

[51] Int. Cl.⁶ ..................................................... B29C 49/08
[52] U.S. Cl. ............................ 264/529; 264/573; 604/96; 606/194
[58] Field of Search ................... 604/96; 606/194; 264/529, 520, 521, 532, 573

[56] References Cited

U.S. PATENT DOCUMENTS

| | | |
|---|---|---|
| 2,307,817 | 1/1943 | Austin . |
| 4,522,867 | 6/1985 | Hill, Jr. et al. . |
| 4,721,654 | 1/1988 | Richardson et al. . |
| 4,906,244 | 3/1990 | Pinchuk et al. . |
| 4,938,676 | 7/1990 | Jackowski et al. . |
| 4,963,313 | 10/1990 | Noddin et al. ............................ 264/573 |
| 4,970,274 | 11/1990 | Chacko et al. . |
| 5,017,325 | 5/1991 | Jackowski et al. . |
| 5,055,024 | 10/1991 | Jackowski et al. . |
| 5,087,394 | 2/1992 | Keith ....................................... 264/532 |
| 5,108,415 | 4/1992 | Pinchuk et al. . |
| 5,156,612 | 10/1992 | Pinchuk et al. . |
| 5,223,205 | 6/1993 | Jackowski et al. . |
| 5,236,659 | 8/1993 | Pinchuk et al. . |
| 5,304,197 | 4/1994 | Pinchuk et al. . |
| 5,304,340 | 4/1994 | Downey . |
| 5,328,468 | 7/1994 | Kaneko et al. . |
| 5,330,428 | 7/1994 | Wang et al. . |
| 5,334,146 | 8/1994 | Ozasa . |
| 5,348,538 | 9/1994 | Wang et al. . |
| 5,356,591 | 10/1994 | Pinchuk et al. . |
| 5,403,340 | 4/1995 | Wang et al. . |
| 5,449,371 | 9/1995 | Pinchuk et al. . |
| 5,500,180 | 3/1996 | Anderson et al. . |
| 5,500,181 | 3/1996 | Wang et al. . |
| 5,556,383 | 9/1996 | Wang et al. . |
| 5,714,110 | 2/1998 | Wang et al. ............................. 264/529 |
| 5,807,520 | 9/1998 | Wang et al. ............................. 264/529 |

Primary Examiner—Catherine Timm
Attorney, Agent, or Firm—Daniel W. Latham; Harold R. Patton

[57] ABSTRACT

A method for making a medical balloon catheter in a single molding operation employs a parison which is molded and biaxially oriented by the use of first and second pressurization stages. The starting material is in the form of a tubular parison with a reduced diameter portion which is made of a biaxial orientable polyamide or polyetheramide material. The resulting balloon can be attached to a catheter that includes a tapered or stepped distal end without further shaping or modification of the balloon ends.

19 Claims, 3 Drawing Sheets

METHOD FOR MAKING MEDICAL BALLOON CATHETER

BACKGROUND OF THE INVENTION

This invention relates to balloon catheters which are especially useful in medical dilatation procedures.

Balloon catheters have been found to be useful for the relief of arterial stenosis as in percutaneous transluminal angioplasty (PTA) and percutaneous transluminal coronary angioplasty (PTCA) procedures and in many other medical applications involving not only insertion into blood vessels but also involving insertion into a variety of body cavities. Balloons can be made from a variety of commercially available materials which are generally of the thermoplastic polymeric type. Included among the known materials are polyolefins, poly(vinyl chloride), polyethylene terephthalate, polyamides, polyetheramides and the like. Balloons made from such materials exhibit the properties of the materials from which they are made. For example, toughness, flexibility, tensile strength, and elasticity are properties which can be produced in balloons from off-the-shelf polymeric materials. For example, polyamides were thoroughly characterized in their structure and properties and disclosed in various patents of the DuPont company in the late 1930's and early 1940's. One such property is their ability to make high strength, thin-walled balloon structures by blowing and stretching a tube in a mold to produce biaxial orientation of the material as disclosed in U.S. Pat. No. 2,307,817 issued to Austin. The same balloon materials have been used to make balloons for medical catheters as disclosed in U.S. Pat. No. Re. 32,983 issued to Levy or U.S. Pat. No. 5,055,024 issued to Jackowski et al.

The specific processing steps required to make such biaxially oriented products is well established in the art of plastic bottle making. For example, in U.S. Pat. No. 4,721,654 issued to Richardson et al, a parison of a copolyamide material is subjected to stretching and internal pressure in a mold by which the material is radially and longitudinally stretched to produce a biaxial orientation. The molded product is then annealed in the mold at its final shape to increase the crystallinity of the material. This is accomplished by maintaining pressure inside the molded article and contacting the article against the heated mold for the time required to heat set the material. In the making of a medical balloon, this process may be adopted with various modifications and additional steps required to produce a suitable balloon shape. For example, in U.S. Pat. No. 5,334,146 issued to Ozasa, a catheter balloon is made by forming a tubular parison made of a drawable polymer, heating the parison at a temperature in the range from the second-order transition temperature to the first-order transition temperature of the polymer used, and then stretching it in the direction of its axis and then inflating it radially while heated. The stretched and inflated parison is then cooled below the second-order transition temperature of the polymer, and then deflated. The resulting balloon has a cylindrical portion of a substantially uniform desired diameter and desired wall thickness but tapered portions of a wall thicknesses which are thicker than desired thicknesses at the front and rear of the cylindrical portion and at the connecting portions at the front and the rear of the tapered portions. Therefore, the balloon is subjected to a redrawing operation in the tapered portions of the balloon to reduce their wall thicknesses to desired thicknesses by stretching the tapered portions in the direction of the axis of the balloon. However, the disclosed method of redrawing requires additional processing steps which are undesirable in a mass-production balloon. It is therefore an object of the invention to form the balloon in a single molding process in which the cylindrical portion of the balloon, the tapered portions of the balloon and the connecting portions of the balloon are all formed in a single molding operation which makes the balloon ready for attachment to the catheter.

SUMMARY OF THE INVENTION

We have discovered a method for making a medical balloon catheter in a single molding operation in which a series of molding steps are performed within the mold. The starting material is in the form of a parison which can be made from a length of extruded tubing made of a biaxial orientable polyamide or polyetheramide material. For example, the tubing can be a nylon or polyether block amide material having 6 to 12 carbons in the repeating unit. The parison can be made by longitudinally stretching a portion of the tubing such that the diameter of the tubing is necked-down in diameter in that portion of the tubing when compared with the rest of the tubing. For example, the necked-down diameter can be about 40–85% of the diameter of the rest of the tubing. The parison is placed into a mold having several sections. The first section is a generally cylindrical section forming the a distal attachment portion of the balloon. A second, intermediate portion of the mold also has a generally cylindrical configuration but has a larger diameter which forms the central portion of the balloon. A third generally cylindrical section of the mold forms the proximal attachment portion of the balloon. This third or proximal section is larger than the first cylindrical section in order to allow the balloon to conform to the shape of the catheter which generally has a larger outer diameter at the proximal attachment point. The intermediate portion of the mold is, of course, larger than either the first, distal section or the third, proximal section of the mold. The mold also includes smooth, tapering transitions between the cylindrical sections of the mold with the preferred form being a conical taper or cone which would be provided at each transition. The parison is sized so that the full diameter of the tubing is larger in outer diameter than the inner diameter of the first, distal portion of the mold but is smaller in outer diameter than the inner diameter of the third, proximal portion of the mold. The relation between the size of the intermediate portion of the mold and the parison is such that the parison can be oriented to a hoop strength in the range of about 15,000–35,000 psi—typically the mold being 5 to 8 times larger in internal diameter than the interior diameter of the parison.

The parison is placed into the mold such that a portion of the necked-down portion of the tubing resides within the first, distal portion of the mold and a portion of the full diameter tubing resides within the intermediate and proximal mold portions. Preferably, the parison includes a relatively abrupt transition between the original diameter and the necked-down diameter so that the parison can be inserted into the mold until the transition rests against the opening to the first, distal section of the mold. The ends of the parison extend out of the mold such that they can be clamped and such that a pressurized fluid can be admitted into the parison. Once the parison is secured in the mold, a first pressure is applied into the tubing. A pressure in the range of about 300–450 psi is generally sufficient. The tubing is then heated in the mold to a temperature above a glass transition temperature of the material. Although the heating temperature will depend on the material, a temperature in the range of about 220–285° F. will generally suffice. The tubing is then longitudinally stretched at a controlled velocity and distance which thins out the material thickness in the parison to the point where it will radially expand at the temperature and pressure in the parison. The material of the parison is thus biaxially oriented. Generally, it is desirable to have a short dwell time at the balloon forming temperature to ensure that the tubing has reached a uniform temperature before the stretching step commences. Generally, the dwell time should be at least 5 seconds after the desired temperature set point has been reached. The longitudinal stretching then commences for a preset rate and distance. Preferably both ends of the parison are stretched simultaneously to about the same distance. The rate of stretching may be varied to maintain a uniform position and stretch of the portion of the parison within the mold. Typically, the necked-down portion of the parison will be stretched at a slightly higher rate. The total amount of stretch will depend on the material characteristics and the desired strength and wall thickness for the balloon. Typically a stretch of about 4–7 times the length of the balloon may be applied. A second, higher pressure is then applied into the biaxially oriented tubing in order to complete the formation of the balloon by pressing the tubing against the tapering cone sections of the mold or against any other small details which are to be applied by the mold. Typically, this pressure is about 15–40% higher than the pressure at which the parison was initially expanded and stretched. Preferably, the balloon so formed can also be annealed in the mold at the same time as the high pressure forming to increase crystallinity and reduce internal stresses within the material. The parison is therefore kept in contact with the mold for a period of time and under conditions which will increase the crystallinity of the material. This typically involves increasing the temperature of the material to a temperature higher than the temperature at which the parison was drawn but well below the crystalline melting temperature of the material. Typically, this temperature will be in the range of about 250° F. to 310° F. depending on the material being used and the expansion temperature selected. The balloon is then cooled while still under pressure in the mold to a temperature below the glass transition temperature of the material. It can then be removed from the mold. The balloon can then be attached by attaching the cooled tubing to a distal end of a catheter body. Since the distal attachment portion of the balloon is smaller in inside diameter than the inside diameter of the proximal attachment portion of the balloon, the balloon can be attached to a catheter that includes a tapered or stepped distal end without further shaping or modification of the balloon attachment portions.

DETAILED DESCRIPTION OF THE PREFERRED EMBODIMENTS

This invention relates to a method for making a medical balloon catheter in a single molding operation in which a series of molding steps are performed within a single mold.

Figure 1:
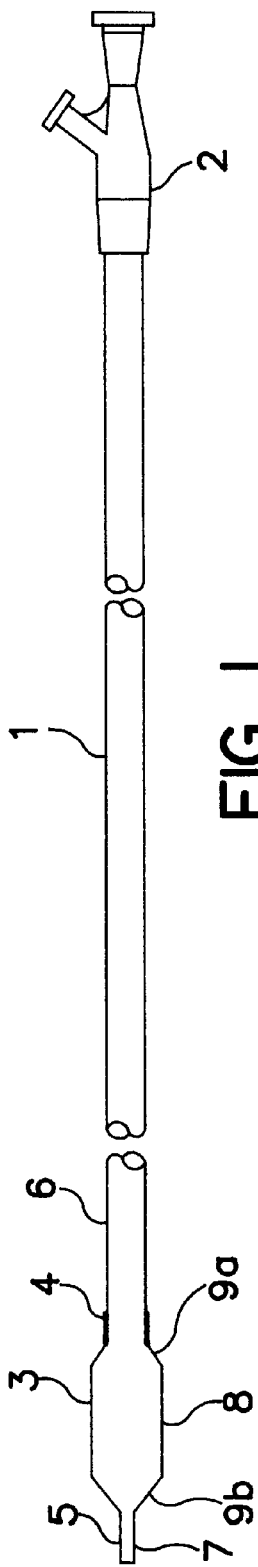
FIG. 1 is a side view of a balloon catheter made according to the present invention.
Figure 2:
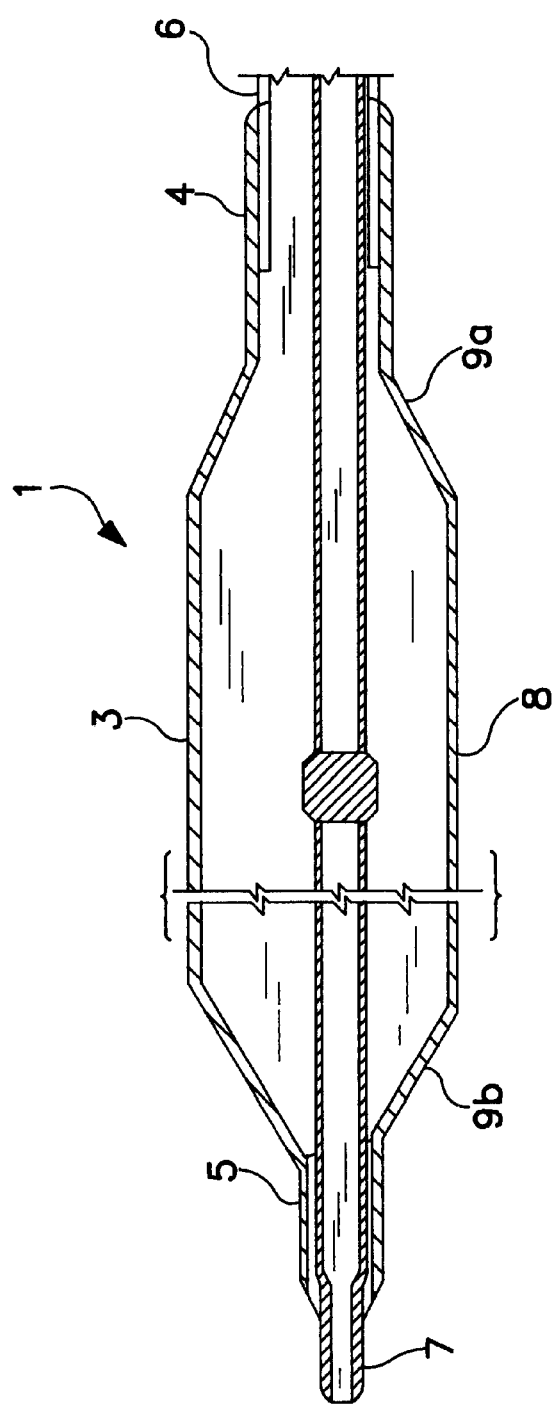
FIG. 2 is a side sectional view of the distal end of the catheter of FIG. 1.

Referring now to FIGS. 1 and 2, the balloon catheter 1 made according to the present invention has a conventional appearance with a hub 2 at a proximal end of the catheter 1 and a balloon 3 at a distal end of the catheter 1. The balloon 3 has a proximal end 4 by which the balloon 3 is attached at a proximal end to a tube 6 of the catheter 1. The balloon 3 also has a distal end 5 by which the balloon 3 is attached to a second tube 7 of the catheter 1. The balloon 3 is also shown with a central, cylindrical portion 8 and proximal and distal cone portions 9a and 9b. The attachment of the balloon 3 to the catheter 1 can be made by adhesive, thermal bonding or other conventional methods.

Figure 3:
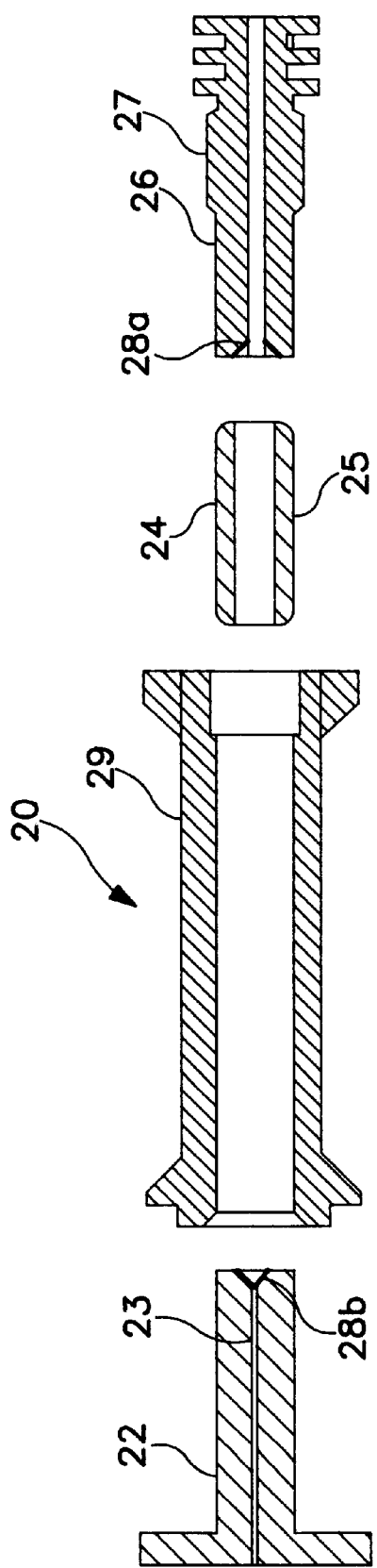
FIG. 3 is an exploded side sectional view of a mold assembly for making a balloon according to the invention.
Figure 4:
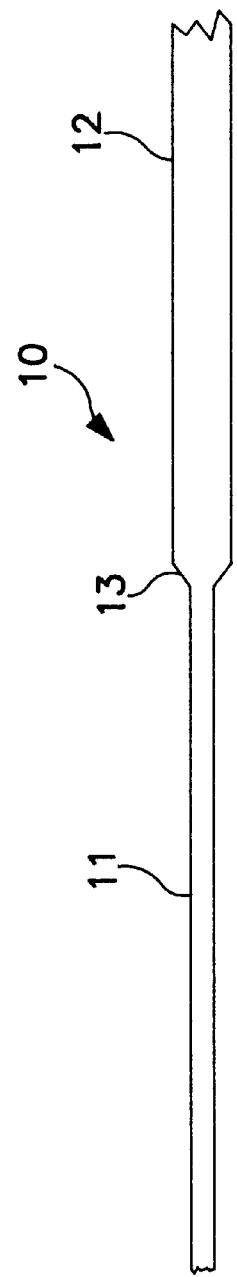
FIG. 4 is a partial side view of a parison for making a balloon according to the present invention.

Referring now also to FIGS. 3 and 4, the starting shape is in the form of a parison 10 made from a length of extruded tubing made of a biaxial orientable polyamide or polyetheramide material. The parison 10 is made by longitudinally stretching a portion of the tubing such that the tubing has a portion 11 with a necked-down diameter and a full diameter in another portion 12 of the tubing. For example, the necked-down diameter portion 11 can be about 40–85% of the full diameter portion 12 of the tubing. The parison 10 preferably includes a relatively abrupt transition 13 between the original diameter portion 12 and the necked-down diameter. The parison 10 is placed into a mold 20 having several sections. The first section 22 is a generally cylindrical section having a bore 23 therethrough forming the a distal attachment portion 5 of the balloon 3. A second, intermediate portion 24 of the mold 20 also has a generally cylindrical configuration but has a larger diameter bore 25 which forms the central portion 8 of the balloon 3. A third generally cylindrical portion 26 of the mold 20 has a bore 27 therethrough which forms the proximal attachment portion 4 of the balloon 3. The bore 27 of the third or proximal portion 26 is larger than the bore 23 of the first cylindrical portion 22 in order to allow the balloon 3 to conform to the shape of the catheter 1 which generally has a larger outer diameter at the proximal attachment 4. The intermediate portion 24 of the mold 20, of course, has a larger bore 25 than either the bore 23 of the first, distal portion 22 or the bore 27 of the third, proximal portion 26 of the mold 20. The mold also includes smooth, tapering transitions 28a, 28b between the cylindrical sections 22, 24, 26 of the mold 20 with the preferred form being a conical taper or cone which would be provided at each transition 28a, 28b. The parison 10 is sized so that the full diameter portion 12 is larger in outer diameter than the bore 23 of the first, distal portion 22 of the mold 20 but is smaller in outer diameter than the bore 27 in the third, proximal portion 26 of the mold 20. Preferably, the full diameter portion 12 is about 10 to 50% smaller than the bore 27 in the proximal portion 26 and the necked-down portion is about 10 to 50% smaller than the bore 23 of the first, distal portion 22 in order to ensure proper centering of the parison 10 within the mold 20. The relation between the size of the intermediate portion 24 of the mold 20 and the parison 10 is such that the parison 10 can be oriented to a hoop strength in the range of about 15,000–35,000psi—typically the bore 25 of the mold 20 being 5 to 8 times larger in internal diameter than the internal diameter of the full diameter portion 12 of the parison 10. The mold 20 is assembled by inserting the intermediate portion 24 centrally into a housing 29 and also inserting the distal portion 22 and proximal portion 26 into the housing 29 such that the three mold sections 22, 24, 26 are in abutting relation.

Figure 5:
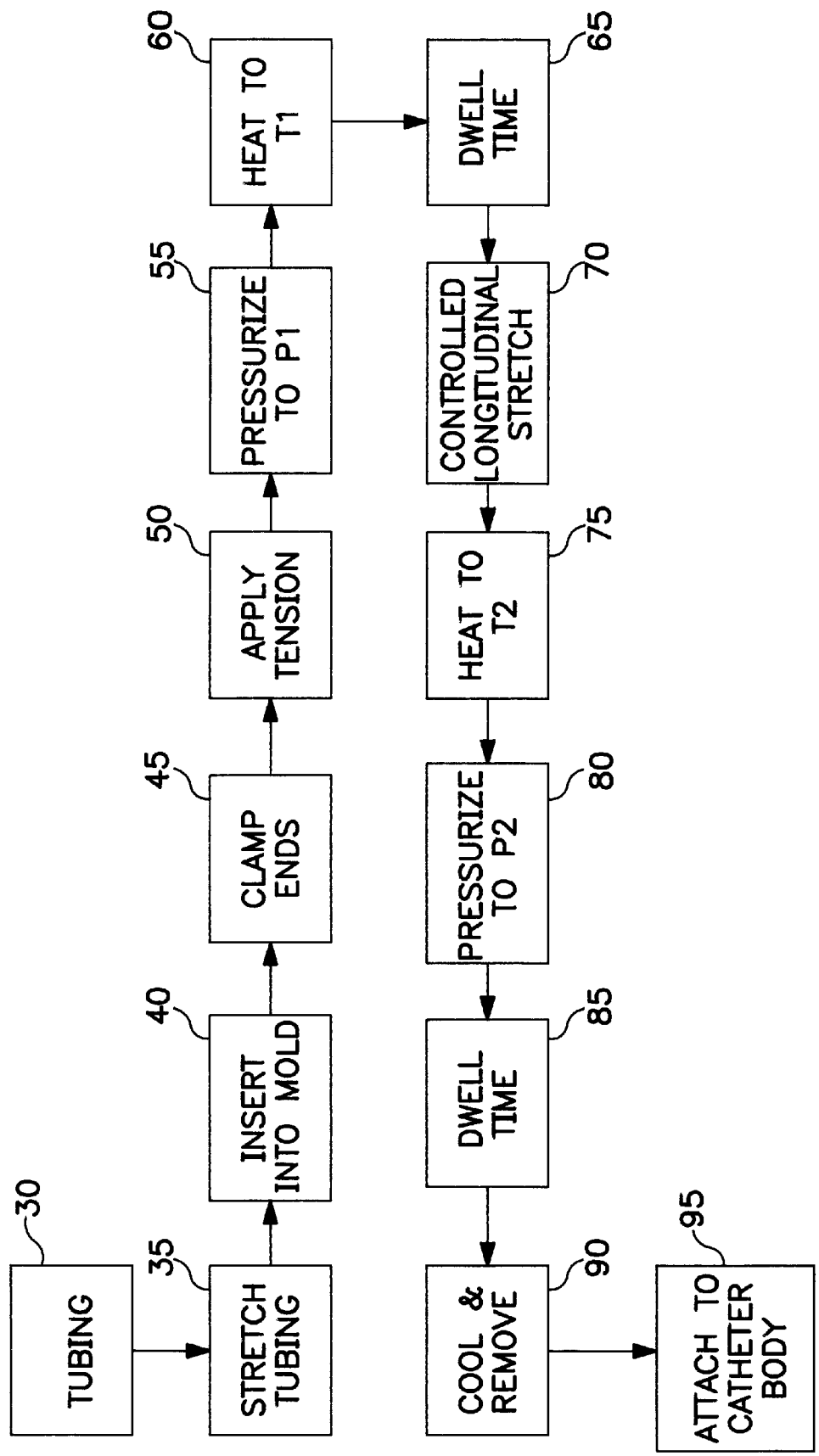
FIG. 5 is a flow chart of the method of the present invention.

Referring now also to FIG. 5, extruded thin wall tubing 30 is stretched 35 to form a parison 10. This stretching can be performed on the tubing at room temperature or after the tubing has been heated. The resulting parison 10 is inserted 40 into the mold 20 such that a portion of the necked-down portion 11 of the parison 10 resides within the bore 23 of the first, distal portion 22 of the mold 20 and a portion of the full diameter 12 resides within the bores 25, 27 of the intermediate and proximal mold portions 24, 26 until the transition 13 rests against the opening of the bore 23 to the first, distal portion 22 of the mold 20. The ends of the parison 10 then extend out of the mold 20 such that they can be clamped 45 and lightly tensioned 50 such that a pressurized fluid can be admitted into the parison 10. Once the parison 10 is secured in the mold 20, and clamped 45 and tensioned 50, a first pressure (P1) is applied 55 into the parison 10. A pressure in the range of about 300–450 psi is generally sufficient. The parison 10 is then heated in the mold 20 to a preset temperature (T1) 60 above a glass transition temperature of the material such that the parison 10 is both heated to T1 and pressurized within the mold 20 at the first pressure P1. Although the heating temperature T1 will depend on the material, a temperature in the range of about 220–285° F. will generally suffice. Once the preset temperature T1 has been reached, the parison 10 is then longitudinally stretched 70 to cause the biaxial orientation of the material. The longitudinal stretching 70 causes the parison 10 to simultaneously expand as the wall of the parison 10 becomes thinned-out and less resistant to radial expansion. Generally, before the stretching 70 commences it is desirable to have a short dwell time 65 at the preset temperature T1 in order to ensure that the parison 10 has reached substantial temperature uniformity at the preset temperature T1. Generally, the dwell time 65 should be at least 5 seconds and preferably 10 seconds after the desired temperature set point T1 has been reached. The longitudinal stretching 70 then commences for a preset rate and distance.

Preferably both ends of the parison 10 are stretched simultaneously to about the same distance. The rate of stretching 70 may be varied to maintain a uniform position and stretch of the portion of the parison 10 within the mold 20. Typically, the necked-down portion 11 of the parison 10 will be stretched at a slightly higher rate. The total amount of stretch applied in the longitudinal stretch 70 will depend on the material characteristics and the desired strength and wall thickness for the balloon. Typically a longitudinal stretch 70 of about 4–7 times the length of the balloon 3 may be applied.

It will be appreciated that during the longitudinal stretch 70, the portion 11 of the parison 10 which was initially stretched from the tubing 30 will be pulled out of the mold 20 and will not be incorporated into the balloon 3. Thus, the necked-down portion 11 of the parison 10 merely constitutes a secure handle from which to draw the balloon and could conceivably be formed in shapes other than drawn tubing. A second, higher pressure (P2) is then applied 80 into the biaxially oriented parison in order to complete the formation of the balloon 3 by pressing the parison against the tapering cone sections 28a, 28b of the mold 20. Typically, this pressure is about 15–40% higher than the pressure at which the parison 10 was initially expanded and stretched. If desired, the balloon 3 so formed can be annealed in the mold 20 as pressure P2 is applied to reduce internal stresses within the material by heating the fully blown parison to a temperature T2 75 which is typically higher than the molding temperature T1 and which is sufficient to increase crystallinity and reduce stresses within the material. Typically, this temperature T2 will be in the range of about 250° F. to 310° F. depending on the material being used and the expansion temperature T1 which was selected. Again, it is desirable to apply a dwell time 85 to relieve stresses and develop crystallinity in the parison 10 as the parison 10 is pressed against the mold 20. The dwell time 85 required will depend on the temperature of the mold 20 and the requirements of the material being used. Generally, a dwell time of at least 5 seconds and preferably 10 seconds is applied after pressure P2 has been reached. The parison, now in the shape of balloon 3, is then cooled 90 while still under pressure in the mold 20 to a temperature below the glass transition temperature of the material. The balloon 3 is then removed from the mold 20. The balloon 3 can then be attached 95 by removing the excess portions of the parison at the ends of the balloon and then bonding it to a distal end of a catheter body. Since the distal attachment portion 5 of the balloon 3 is formed to be smaller in inside diameter than the inside diameter of the proximal attachment portion 4 of the balloon 3 and since the balloon 3 is formed to tight tolerances at attachment portions 4, 5, the balloon 3 can be attached to a catheter 1 that includes a tapered or stepped distal end without further shaping or modification of the balloon attachment portions 4, 5. Also, depending on the tolerances required in the method for bonding the balloon to the catheter, the diameter of the ends can be adjusted by inserting a mandrel of the precise diameter required into an end of the balloon and heating just the end portion briefly to ensure the correct size of the portion to be bonded. Once attached to the catheter 1, the balloon 3 can be folded and heat set on the catheter 1 at about human body temperature of 37° C. to ensure that the balloon 3 is dimensionally stabilized for use at that temperature. It will be appreciated that many of these steps may be performed by automated or semi-automated equipment as is well known by those skilled in the art such that the process can be completed at a low per unit cost. The following examples further describe the method of the invention:

EXAMPLE

A balloon of 3.0 mm rated diameter and 20 mm rated length was made by the method of the invention. A parison was made from extruded tubing of a polyether block amide copolymer sold under the trade name Pebax 7233 (Atochem North America, Inc., Philadelphia Pa.). The tubing had an internal diameter of 0.017 and an outer diameter of 0.041. A portion of the tubing was drawn to a diameter of about 50% of the initial tubing diameter. The resulting parison was placed into a mold having a nominal bore at the distal portion of the mold of 0.0335 inch, at the intermediate portion of the mold of 0.1181 inch and at the proximal end of the mold of 0.0430 inch. An automated sequence was then started which (1) closed clamps on each end of the parison and tensioned the parison lightly (2) pressurized the parison to 340 psi with nitrogen (3) heated the parison in the mold by applying steam from a boiler toward a set point of 253° F. (steam was applied until an indicated temperature of 248° F. was achieved and the system was then allowed to rise to the set point without overshooting the intended temperature) (4) applied a dwell time of 10 seconds (5) simultaneously moved the distal and proximal clamps in opposite directions to stretch the parison (2.7 inches at a rate of 56 inches/minute on the distal portion of the the parison and 2.8 inches at a rate of 46 inches/minute on the proximal portion of the parison) (6) additionally heated the parison in the mold by raising the temperature set point to 273° F. (steam was applied until an indicated temperature of 268° F. was achieved and the system was then allowed to rise to the set point) (7) increased the pressure in the parison to 500 psi (8) maintained the temperature and pressure for a dwell time of 10 seconds and (9) cooled the balloon in the mold under pressure. The balloon was then removed from the mold. The balloons made by this method had an average double wall thickness of about 1.50 mils, an average burst pressure of about 340 psi and reached their rated inflation diameter at about 120 psi.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for making a medical balloon catheter comprising the steps of:

providing a parison comprising a length of tubing comprising a biaxially orientable polyamide or polyetheramide material, the parison having a first portion having a first outer diameter and a second portion having a second, smaller outer diameter; providing a mold having a generally cylindrical shape having a first, distal portion having a first mold diameter, a second, intermediate portion having a second mold diameter and a third, proximal portion having a third mold diameter, the first mold diameter being smaller than the first outer diameter of the parison and larger than the second, smaller outer diameter of the parison;

placing the parison in the mold such that a portion of the second, smaller diameter portion of the parison resides within the first, distal portion of the mold and a portion of the first portion of the parison resides within the intermediate and proximal mold portions;

applying a first pressure into the parison in the mold;

heating the pressurized parison in the mold to a preset temperature above a glass transition temperature of the material;

longitudinally stretching the pressurized, heated parison within the mold such that the parison also expands in a radial direction within the mold at the first pressure during the longitudinal stretching;

applying a second, higher pressure into the longitudinally stretched, heated parison within the mold;

cooling the stretched parison while in the mold under pressure to a temperature below the glass transition temperature of the material; and attaching the cooled parison as a balloon to a distal end of a catheter body.

2. The method of claim 1 wherein the biaxially orientable polyamide or polyetheramide has an amide repeating unit of 6 to 12 carbon atoms in length.

3. The method of claim 2 wherein the biaxially orientable material is a nylon.

4. The method of claim 2 wherein the biaxially orientable material is a polyether block amide.

5. The method of claim 1 wherein the parison is made from the length of tubing by stretching a portion of the length of tubing to the second, smaller outer diameter which is between about 40% and 85% of the diameter of the first outer diameter.

6. The method of claim 1 wherein the mold includes in the intermediate portion a first, tapering portion at a first end of the intermediate portion and a second, tapering portion at a second end of the intermediate portion.

7. The method of claim 6 wherein the first and second tapering portions are conical tapers.

8. The method of claim 5 wherein the tubing is longitudinally stretched to make an abrupt transition between the first and second portions of the parison.

9. The method of claim 8 wherein the stretched portion of the tubing is placed into the mold such that the transition rests against an opening to the first, distal portion of the mold.

10. The method of claim 1 wherein the first pressure is in the range of about 300 psi to 450 psi.

11. The method of claim 1 wherein the pressurized parison is heated to a temperature in the range of about 220° F. to 285° F. prior to stretching the parison.

12. The method of claim 1 wherein the pressurized parison is heated to the preset temperature for a period of at least 5 seconds prior to stretching the parison.

13. The method of claim 1 wherein the second, higher pressure is about 15% to 40% greater than the first pressure.

14. The method of claim 1 wherein the second, higher pressure is applied for at least about 5 seconds after the parison is stretched.

15. The method of claim 1 wherein the catheter body has a first portion with a first outer diameter and a second portion with a second, smaller outer diameter and wherein the cooled parison has a first end portion having a first inner diameter and a second end portion having a second, smaller inner diameter and wherein the first end portion of the cooled parison is attached at the first portion of the catheter and the second end portion of the cooled tubing is attached at the second portion of the catheter.

16. The method of claim 1 wherein the stretched parison at the second pressure is heated to a second, higher temperature by which the parison is annealed to reduce internal stresses.

17. The method of claim 16 wherein the second, higher temperature by which the parison is annealed is a temperature in the range of about 250° F. to 310° F.

18. The method of claim 1 wherein, prior to radial expansion, the second, smaller, outer diameter of the second portion of the parison is between about 40% and 85% of the diameter of the first outer diameter of the first portion of the parison.

19. The method of claim 1 wherein, prior to radial expansion, the parison comprises an abrupt transition between the first and second portions of the parison.

* * * * *